US007652076B2

(12) United States Patent
Schlueter et al.

(10) Patent No.: US 7,652,076 B2
(45) Date of Patent: Jan. 26, 2010

(54) OPHTHALMIC AND OTORHINOLARYNGOLOGICAL DEVICE MATERIALS

(75) Inventors: Douglas C. Schlueter, Azle, TX (US); Mutlu Karakelle, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 660 days.

(21) Appl. No.: 11/451,097

(22) Filed: Jun. 12, 2006

(65) Prior Publication Data

US 2006/0282163 A1    Dec. 14, 2006

Related U.S. Application Data

(60) Provisional application No. 60/690,000, filed on Jun. 13, 2005.

(51) Int. Cl.
*G02B 1/04* (2006.01)
*A61F 2/16* (2006.01)

(52) U.S. Cl. ............ 523/106; 526/318.1; 526/319; 526/320; 526/321; 526/326; 526/328.5; 623/6.11; 623/6.58; 623/6.6

(58) Field of Classification Search ............ None
See application file for complete search history.

(56) References Cited

U.S. PATENT DOCUMENTS

| | | | |
|---|---|---|---|
| 3,390,206 A | 6/1968 | Thompson | 260/875 |
| 3,842,059 A | 10/1974 | Milkovich et al. | 260/486 |
| 3,862,077 A | 1/1975 | Schulz et al. | 260/29.6 |
| 4,085,168 A | 4/1978 | Milkovich et al. | 260/886 |
| 5,057,366 A | 10/1991 | Husman et al. | 428/355 |
| 5,278,244 A | 1/1994 | Babu | 525/292 |
| 5,290,892 A | 3/1994 | Namdaran et al. | 526/259 |
| 5,331,073 A | 7/1994 | Weinschenk, III et al. | 526/264 |
| 5,470,932 A | 11/1995 | Jinkerson | 526/312 |
| 5,693,095 A | 12/1997 | Freeman et al. | 623/6 |
| 5,708,094 A | 1/1998 | Lai et al. | 525/296 |
| 5,763,548 A | 6/1998 | Matyjaszewski et al. | 526/135 |
| 5,789,487 A | 8/1998 | Matyjaszewski et al. | 525/301 |
| 5,852,129 A | 12/1998 | Kusakabe et al. | 525/330.3 |
| 6,083,856 A | 7/2000 | Joseph et al. | 442/361 |
| 6,162,882 A | 12/2000 | Matyjaszewski et al. | 526/111 |
| 6,174,546 B1 | 1/2001 | Therriault et al. | 424/448 |
| 6,353,069 B1 | 3/2002 | Freeman et al. | 526/319 |
| 6,369,164 B1 | 4/2002 | Klee et al. | 525/285 |
| 6,737,496 B2 | 5/2004 | Hodd et al. | 528/32 |
| 6,787,584 B2 | 9/2004 | Jia et al. | 523/115 |
| 6,806,337 B2 | 10/2004 | Schlueter et al. | 526/318.43 |
| 6,824,266 B2 | 11/2004 | Jethmalani et al. | 351/159 |
| 6,872,793 B1 | 3/2005 | Schlueter | 526/326 |
| 2003/0176521 A1 | 9/2003 | Jethmalani et al. | 522/46 |

FOREIGN PATENT DOCUMENTS

| | | |
|---|---|---|
| GB | 1096912 | 12/1997 |
| WO | WO 03/040154 | 5/2003 |
| WO | WO 2004/007579 | 1/2004 |

OTHER PUBLICATIONS

Acar, "Adventitious Effect of Air in Atom Transfer Radical Polymerization: Air-Induced (Reverse) Atom Transfer Radical Polymerization of Methacrylates in the Absence of an Added Initiator," *Macromolecules*, vol. 33, pp. 7700-7706 (2000).
Antolin et al., "Synthesis of poly (t-butyl acrylate) macromonomers," *Polymer*, vol. 31, pp. 967-970 (1990).
Bandermann et al., "Functionalized initiators for gorup transfer and metal-free anionic polymerization for the synthesis of macromonomers: overview and new results," *Macromol. Chem. Phys.*, vol. 196, pp. 2335-2347 (1995).
Boonstra, "Role of particulate fillers in elastomer reinforcement: a review," *Polymer*, vol. 20, pp. 691-704 (1979).
Bryant et al., "Synthesis and Characterization of Photopolymerized Multifunctional Hydrogels: Water-Soluble (Vinyl Alcohol) and Chondroitin Sulfate Macromers for Chondrocyte Encapsulation," *Macromolecules*, vol. 37, pp. 6726-6733 (2004).
Gu et al., "Preparation of High Strength and Optically Transparent Silicone Rubber," *European Polymer Journal*, vol. 34(1), pp. 1727-1733 (1998).
Haddleton et al., "Monohydroxy terminally functionalised poly(methyl methacrylate) from atom transfer radical polymerisation," *Chem. Commun.*, 1997, pp. 683-684.
Hatada et al., "Preparation of a uniform poly(methyl methacrylate) macromonomer and its polymerization," *Macromol. Rapid Commun.* vol. 18, pp. 37-43 (1997).
Henschke et al., "Metallocene-Catalyzed Copolymerization of Propene with Polystyrene Macromonomers," *Macromolecules*, vol. 30 (26), pp. 8097-8100 (1997).
Ito., "Polymeric Design by Macromonomer Technique," *Prof. Polymer Science*, vol. 23, pp. 581-620 (1998).
Kato et al., "Polymerization of Methyl Methacrylate with the Carbon Tetrachloride/Dichlorotris-(triphenylphosphie)ruthenium (II)/ Methylaluminum Bis (2,6-di-tert-butylphenoxide) Initiating System: Possibility of Living Radical Polymerization," *Macromolecules*, vol. 28, pp. 1721-1723 (1995).
Kennedy, "New Biomaterials by Carbocationic Processes," *Macromol. Symp.*, vol. 85, pp. 79-96 (1994).
Lutz et al., :Anionic Polymerization, *Polymer Bulletin*, vol. 12, pp. 79-85 (1984).
Norman et al., "Synthesis of Well-Defined Macromonomers by Sequential ATRP—Catalytic Chain Transfer and Copolymerization with Ethyl Acrylate," *Macromolecules*, vol. 35, pp. 8954-8961 (2002).
Radke et al., "Acrylic Thermoplastic Elastomers and Comb-Shaped Poly(methyl methacrylate) via the Macromonomer Tecnique," *Macromol. Symp.*, vol. 101, pp. 19-27 (1996).
Sarbu et al., "Syntheses of Hydroxy-Telechelic Poly(methyl acrylate) and Polystyrene by Atom Transfer Radical Coupling," *Macromoleculesl*, vol. 37I, pp. 9694-9700 (2004).
Sawhney et al. "BioerodibleHydrogels Based on Photopolymerized Poly(ethylene glycol)-co-poly(α-hydroxy acid) Diacrylate Macromers," *Macromolecules*, vol. 26, pp. 581-587 (1993).
Schon et al., "New Strategy for the Synthesis of Halogen-Free Acrylate Macromonomers by Atom Transfer Radical Polymerization," *Macromoleculesl*, vol. 34, pp. 5394-5397 (2001).

(Continued)

*Primary Examiner*—David Wu
*Assistant Examiner*—Vu Nguyen
(74) *Attorney, Agent, or Firm*—Scott A. Chapple

(57) ABSTRACT

Disclosed are soft, high refractive index device materials having improved strength. The materials contain a monofunctional or difunctional, acrylate or methacrylate terminated aromatic functional methacrylic or acrylic macromer.

19 Claims, No Drawings

OTHER PUBLICATIONS

Schulz et al., "Graft Polymers with Macromonomers. I. Synthesis from Methacrylate-Terminated Polystyrene," *J. of Applied Polymer Science*, vol. 27, pp. 4773-4786 (1982).

Schulz et al., "Graft Polymers with Macromonomers. II. Copolymerization Kinetics of Methacrylate-Terminated Polystyrene and Predicted Graft Copolymer Structures," *J. of Polymer Sciencel*, vol. 22, pp. 1633-1652 (1984).

Shen et al., "A simplified wittig synthesis using polyacrylates with a terminal triphenylphosphonium group and polymerization f the macromonomers," *Makromol. Chem.*, vol. 193, pp. 743-748 (1992).

Shen et al., "Versatile Initiators for Macromonomer Syntheses of Acrylates, Methacrylates, and Styrene by Atom Transfer Radical Polymerization," *Macromolecule*, vol. 33, pp. 5399-5404 (2000).

Wang et al., "Controlled/Living Radical Polymerization. Halogen Atom Transfer Radical Polymerization Promoted by a Cu(I)/Cu(II) Redox Process," *Macromolecules*, vol. 28, pp. 7901-7910 (1995).

Yamada et al., "Preparation of poly(methyl methacrylate) macromonomer by radical polymerization in the presence of methyl α-(bromomethyl) acrylate and copolymerization of the resultant macromonomer," *Polymer Bulletin*, vol. 35, pp. 423-430 (1991).

Yin et al., "Reactive Blending of Functional PS and PMMA: Interfacial Behavior of in situ Formed Graft Copolymes," *Macromolecules*, vol. 34, pp. 5132-5139 (2001).

Zhang et al., "Synthesis and characterisation of hydroxyl end-capped telechelic polymers with poly (methyl methacrylate)-*block*-poly(*n*-butyl acrylate) backbones via atom transfer radical polymerisation," *Polymer*, vol. 45, pp. 1455-1466 (2004).

OPHTHALMIC AND OTORHINOLARYNGOLOGICAL DEVICE MATERIALS

This application claims priority to U.S. Provisional Application, U.S. Ser. No. 60/690,000 filed Jun. 13, 2005.

FIELD OF THE INVENTION

This invention is directed to improved ophthalmic and otorhinolaryngological device materials. In particular, this invention relates to soft, high refractive index acrylic device materials that have improved strength.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

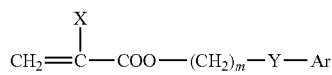

wherein:
X is H or $CH_3$;
m is 0-6;
Y is nothing, O, S, or NR, wherein R is H, $CH_3$, $C_nH_{2n+1}$ (n=1-10), iso-$OC_3H_7$, $C_6H_5$, or $CH_2C_6H_5$; and
Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

The lens materials described in the '095 patent preferably have a glass-transition temperature ("$T_g$") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength, flexibility and non-tacky surface properties to permit IOLs to be inserted through an incision as small as that required for silicone IOLs. The mechanical properties of silicone elastomers are improved by addition of an inorganic filler, typically surface treated silica. Surface treated silica improves the mechanical properties of soft acrylic rubbers, too, but reduces the optical clarity of the finished product. Alternative filler materials having a refractive index closer to soft acrylic rubber are needed.

The addition of reinforcing fillers to soft polymers is known to improve tensile strength and tear resistance. Reinforcement stiffens the polymer and improves its toughness by restricting the local freedom of movement of polymer chains, and strengthens the structure by introducing a network of weak fix points. The reinforcing ability of a particular filler depends upon its characteristics (e.g. size and surface chemistry), the type of elastomer with which it is used, and the amount of filler present. Conventional fillers include carbon black and silicate fillers, where the particle size (for maximum surface area) and wettability (for strength of cohesion) are of primary importance. Covalent chemical bonding between the matrix and the filler is generally not required for effective reinforcement. For a review see: Boonstra, "Role of particulate fillers in elastomer reinforcement: a review" *Polymer* 1979, 20, 691, and Gu, et al., "Preparation of high strength and optically transparent silicone rubber" *Eur. Polym. J.* 1998, 34, 1727.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials contain microphase-separated, domains similar to that found in conventional block copolymers. The presence of the microphase-separated domains improves the strength and influences the surface properties of the polymeric materials without need for added filler. The properties of the materials of the present invention are different than statistical (random) copolymers with identical feed ratios.

DETAILED DESCRIPTION OF THE INVENTION

Unless indicated otherwise, all component amounts are presented on a % (w/w) basis ("wt. %").

The device materials of the present invention are self-reinforced polymeric materials. The materials are copolymers comprising a) a monofunctional acrylate or methacrylate monomer [1], b) a difunctional acrylate or methacrylate cross-linker [2], and c) an acrylate or methacrylate terminated aromatic functional methacrylic or acrylic macromonomer [3] or [4]. In one embodiment, the materials comprise a) a monofunctional acrylate or methacrylate monomer [1], b) a difunctional acrylate or methacrylate cross-linker [2], c) an acrylate or methacrylate terminated aromatic functional methacrylic or acrylic macromonomer [3], and an acrylate or methacrylate terminated aromatic functional methacrylic or acrylic macromonomer [4].

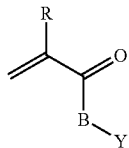
[1]

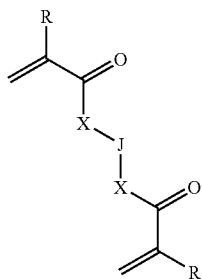
[2]

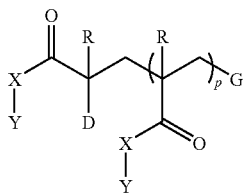
[3]

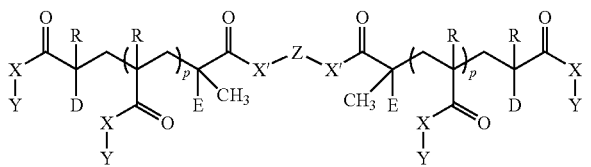
[4]

wherein:
B=$O(CH_2)_n$, $NH(CH_2)_n$, or $NCH_3(CH_2)_n$;
D=Cl, Br, H, or —$CH_2C(=CH_2)C(O)XY$;
E=H or $CH_3$;
G=H, $C(E)(CH_3)C(O)X(CH_2)_nH$, $C(E)(CH_3)C(O)X(CH_2CH_2O)_nCH_3$, or $C(E)(CH_3)C(O)X'Z'X'C(O)C(R')=CH_2$;
R, R' independently=H, $CH_3$, or $CH_2CH_3$;
X, X' independently=$O(CH_2)_n$, $NH(CH_2)_n$, $NCH_3(CH_2)_n$, $O(CH_2CH_2O)_nCH_2$, $O(CH_2CH_2CH_2O)_nCH_2$, $O(CH_2CH_2CH_2CH_2O)_nCH_2$, or nothing;
J=$(CH_2)_a$, $O(CH_2CH_2O)_b$, or nothing;
n=0-6;
Y=$C_6H_5$, $(CH_2)_mH$, $(CH_2)_mC_6H_5$, OH, $CH_2CH(OH)CH_2OH$, $(OCH_2CH_2)_mOCH_3$, or $(OCH_2CH_2)_mOCH_2CH_3$;
m=0-12;
Z, Z' independently=—$(CH_2)_a$—, —$(CH_2CH_2O)_a$—, —$(CH_2CH_2CH_2CH_2O)_a$—, —$C_6H_4$—, —$C_6H_4C(CH_3)(CH_3)C_6H_4$—, or —$[(CH(CH_2CH_3)CH_2)(CH_2CH_2)]_q$—;

a=1-12;
b=1-24;
p=5-400; and
q=1-80.

Free radical polymerization of these ingredients results in a cross-linked polymer network and, depending on the molecular weight of the macromonomer, phase-separated polyacrylate and polymethacrylate domains similar to that found in block copolymers. The phase-separated domains influence the strength and surface properties of the resulting material and produce a copolymer with different material properties than a statistical copolymer with identical feed ratio.

Preferred monomers of formula [1] are those wherein:

R=H, B=$O(CH_2)_2$, Y=$C_6H_5$;

R=H, B=$O(CH_2)_3$, Y=$C_6H_5$; and

R=$CH_3$, B=$O(CH_2)_4$, Y=$C_6H_5$.

Preferred monomers of formula [2] are those wherein:

R=H, X=$OCH_2$, J=$(CH_2)_2$,

R=$CH_3$, X=$OCH_2$, J=nothing; and

R=$CH_3$, X=nothing, J=$O(CH_2CH_2O)_b$, where b>10.

Preferred macromers of formula [3] are those wherein:

R=H or $CH_3$;

G=$C(E)(CH_3)C(O)X'Z'X'C(O)C(R')=CH_2$;

X=$O(CH_2)_n$ and X'=O, where n=1-3;

Y=$C_6H_5$;

E=$CH_3$;

Z and Z'=$(CH_2)_2$; and p is such that the number average molecular weight ($M_n$) of macromer [3] is 5,000-50,000.

Other preferred macromers of formula [3] are those wherein:

R=H or $CH_3$;

D=—$CH_2C(=CH_2)C(O)XY$;

X=$O(CH_2)_n$, where n=1-3

Y=$C_6H_5$;

E=$CH_3$;

Z and Z'=$(CH_2)_2$; and p is such that $M_n$ is 5,000-50,000.

Preferred macromers of formula [4] are those wherein:

R=H or $CH_3$;

X=$O(CH_2)_n$, where n=1-3;

Y=$C_6H_5$;

E=$CH_3$;

D=$CH_2C(=CH_2)C(O)XY$;

X'=O;

Z'=$(CH_2)_2$; and p is such than $M_n$ is 1,000-10,000.

Monomers of formula [1] are known and can be made by known methods. See, for example, U.S. Pat. Nos. 5,331,073 and 5,290,892. Many monomers of formula [1] are commercially available from a variety of sources.

Monomers of formula [2] are known and can be made by known methods, and are commercially available. Preferred monomers of formula (2) include ethylene glycol dimethacrylate; diethylene glycol dimethacrylate; 1,6-hexanediol dimethacrylate; 1,4-butanediol dimethacrylate; poly(ethylene oxide)dimethacrylate (number average molecular weight 600-1000); and their corresponding acrylates.

Macromers of formulas [3] and [4] are known. They are commercially available in some instances and can be made by known methods. Macromonomers of formula [3] and [4] can be made by covalently attaching a polymerizable group to a functional end group of a linear or branched acrylic or methacrylic polymer. For example, hydroxyl terminated poly(methyl methacrylate) may be synthesized by anionic polymerization of methyl methacrylate, then functionalized by termination with ethylene oxide to produce hydroxyl terminated poly(methyl methacrylate). The terminal hydroxyl groups are end-capped on one or both terminal chain ends with an acrylate or methacrylate functionality. The end-caps are covalently attached via known methods, for example esterification with methacryloyl chloride or reaction with an isocyanate to form a carbamate linkage. See, generally, U.S. Pat. Nos. 3,862,077 and 3,842,059, the entire contents of which are incorporated by reference.

Macromers of formula [3] and [4] can also be prepared using atom transfer radical polymerization (ATRP) conditions. For example, a hydroxyl terminal initiator (hydroxyethyl bromoisobutyrate) can combined with copper(I) halide and a solubilizing amine ligand. This can be used to initiate the polymerization of an acrylate or methacrylate monomer. The resulting hydroxyl terminated poly(acrylate) or poly(methacrylate) can then be reacted with methacryloyl chloride or isocyanatoethyl methacrylate. See, generally, U.S. Pat. Nos. 5,852,129, 5,763,548, and 5,789,487.

The flexibility of the copolymeric material of the present invention depends primarily on the glass transition temperature of the homopolymer formed from monomer [1]. The concentration of monomer [1] is typically at least 35%, and preferably 65-85 wt %, of the total (monomer+macromer+cross-linker) concentration. The difunctional cross-linker [2] concentration is typically 10 to 15 wt % of the total concentration when R=$CH_3$, X=nothing, D=$O(CH_2CH_2O)_b$, where b>5, and preferably less than about 3 wt % for lower molecular weight difunctional cross-linkers, for example when R=H, X=$OCH_2$, and D=$(CH_2)_2$.

The materials of the present invention have at least one macromer of [3] or [4], but could have macromers of [3] and [4]. The total amount of macromers [3] and [4] depends on the glass transition temperature of the homopolymer formed from monomer [1] to ensure formation of a flexible polymeric material. The copolymeric materials of the present invention contain a total of at least 5 wt. % of macromers [3] and [4]. For macromers where R=$CH_3$ or $CH_2CH_3$, the total concentration of macromers [3] and [4] is generally below 50 wt. %, and preferably below 35 wt. %. However, for macromers where R=H, the macromer concentration can be increased above 50 wt. % to 65 wt. % or more and still yield a copolymeric material with sufficient flexibility to permit an IOL made of such material to be inserted through a small surgical incision (<2.8 mm). In these cases, where for macromer [3] or [4], R=H and the concentration is greater than 50 wt. %, the viscosity of the mixture of monomer [1], monomer [2] and macromer [3] and/or [4] becomes more important. Macromer loading will also depend upon macromer molecular weight. Macromers [3] and [4] will tend to increase the modulus and decrease the flexibility of the resulting copolymeric material as a function of its molecular weight. At lower molecular weight, macromers [3] and [4] will probably be miscible and the effect on $T_g$ will be more like a conventional copolymer. At higher molecular weight or higher macromer concentration, increased phase separation may occur and allow a distinct macromer phase and two $T_g$'s. In one embodiment, the number average molecular weight of macromer (3) having R=$CH_3$ or $CH_2CH_3$ is 10,000-25,000.

The copolymeric device material of the present invention optionally contains one or more ingredients selected from the group consisting of a polymerizable UV absorber and a polymerizable colorant. Preferably, the device material of the present invention contains no other ingredients besides the monomers of formulas [1] and [2], the macromers [3] and [4], and polymerizable UV absorbers and colorants.

The device material of the present invention optionally contains reactive UV absorbers or reactive colorants. Many reactive UV absorbers are known. A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1-5% (weight). Suitable reactive blue-light absorbing compounds include those described in U.S. Pat. No. 5,470,932. Blue-light absorbers are typically present in an amount from about 0.01-0.5% (weight). When used to make IOLs, the device materials of the present invention preferably contain both a reactive UV absorber and a reactive colorant.

In order to form the device material of the present invention, the chosen ingredients [1], [2], and [3] and/or [4] are combined and polymerized using a radical initiator to initiate polymerization by the action of either heat or radiation. The device material is preferably polymerized in de-gassed polypropylene molds under nitrogen or in glass molds.

Suitable polymerization initiators include thermal initiators and photoinitiators. Preferred thermal initiators include peroxy free-radical initiators, such as t-butyl (peroxy-2-ethyl) hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethylbenzoyldiphenyl-phosphine oxide, commercially available as Lucirin® TPO from BASF Corporation (Charlotte, N.C.). Initiators are typically present in an amount equal to about 5% or less of the total formulation weight, and more preferably less than 2% of the total formulation. As is customary for purposes of calculating component amounts, the initiator weight is not included in the formulation weight % calculation.

The particular combination of the ingredients described above and the identity and amount of any additional components are determined by the desired properties of the finished device material. In a preferred embodiment, the device materials of the present invention are used to make IOLs having an optic diameter of 5.5 or 6 mm that are designed to be compressed or stretched and inserted through surgical incision sizes of 2 mm or less.

The device material preferably has a refractive index in the dry state of at least about 1.47, and more preferably at least about 1.50, as measured by an Abbe' refractometer at 589 nm (Na light source) and 25° C. Optics made from materials having a refractive index lower than 1.47 are necessarily thicker than optics of the same power which are made from materials having a higher refractive index. As such, IOL optics made from materials with comparable mechanical properties and a refractive index lower than about 1.47 generally require relatively larger incisions for IOL implantation.

The material morphology or phase structure will depend on the macromer concentration, molecular weight, it's miscibility in the copolymer network (which also depends on molecular weight), and the polymerization method. The microphase separated behavior can be observed by differential scanning calorimetry (DSC). Microphase-separated materials will exhibit two glass-transition temperatures ("$T_g$"). The continuous phase and non-continuous phase will each exhibit a separate $T_g$. $T_g$ of the continuous phase will primarily determine the material's flexibility properties, and folding and unfolding characteristics, and is preferably less than about +25° C., and more preferably less than about 0° C. $T_g$ of the non-continuous phase has a lesser impact on the materials' flexibility than that of the continuous phase. $T_g$ is measured by differential scanning calorimetry at 10° C./min., and is generally determined at the midpoint of the transition of the heat flux versus temperature curve.

The device material preferably has an elongation of at least 150%, more preferably at 300%, and a Young's modulus of less than 6.0 MPa, more preferably less than 5.0 MPa. These properties indicate that a lens made from such material generally will fold easily and will not crack, tear or split when it is folded. Tensile properties of polymer samples are determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using an Instron Material Tester model 4400 with a 50 N load cell. The grip distance is 14 mm and a crosshead speed is 500 mm/minute and the sample is pulled to failure. The elongation (strain) is reported as a fraction of the displacement at failure to the original grip distance ("Elongation" or "Strain at break %"). The modulus is calculated as the instantaneous slope of the stress-strain curve at 0% strain ("Young's modulus"), 25% strain ("25% modulus") and 100% strain ("100% modulus). Tear resistance was measured on unnicked 90° C. angle specimens (Die C) according to ASTM D624-91 "Standard Test Method for Tear Strength of Conventional Vulcanized Rubber and Thermoplastic Elastomers". The test specimens were 20 mm total length, 9.0 mm guage length and a thickness of 0.9 mm. Testing was performed on samples at standard laboratory conditions of 23±2° C. using an Instron Material Tester model 4400 with a 50 N load cell. The grip distance was 9.0 mm and the crosshead speed was 500 mm/minute and the sample was pulled to failure. The tear resistance ("Tear strength") was calculated from the maximum force obtained during testing divided by the sample thickness.

IOLs constructed of the device materials of the present invention can be of any design capable of being stretched or compressed into a small cross section that can fit through a 2-mm incision. For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

EXAMPLE 1

Synthesis of hydroxyl terminated poly(2-phenylethyl methacrylate)

All synthetic manipulations were performed in a $N_2$-filled glove-box. A Schlenk tube containing a PTFE-coated magnetic stirring bar was charged with 0.3340 g (3.374 mmol) of CuCl, 1.9665 g (11.09 mmol) of N,N,N',N',N"-pentamethyldiethylenetriamine, 30.9268 g (162.57 mmol) of 2-phenylethyl methacrylate (PEMA), and 30 mL of anisole. The flask was warmed to 50° C. in an oil bath and 0.4296 g (2.036 mmol) of 2-hydroxyethyl-2-bromoisobutyrate was added. The reaction was maintained at 50° C. for 3 hrs then cooled to room temperature. The product was diluted with ethyl acetate and purified by column chromatography. The product was further purified by precipitation from acetone into a large excess of methanol at 0° C. The product was isolated by vacuum filtration and rinsed thoroughly with chilled methanol, then dried under vacuum at ambient temperature and resulted in 20.5920 g (67%) of a white solid. The molecular weight was determined by GPC in tetrahydrofuran (THF) against polystyrene standards.

EXAMPLE 2

Synthesis of methacrylate terminated poly(2-phenylethyl methacrylate)macromer [3]

An oven dried Schlenk tube containing a PTFE-coated magnetic stirring bar was flushed with $N_2$ and charged with 20.3434 g (0.97 mmol hydroxyl groups based on GPC $M_n$) of $M_n$ 21,273 hydroxyl terminated poly(PEMA). Anhydrous dichloromethane (50 mL) was added and the polymer was allowed to dissolve. Triethylamine (0.30 mL, 2.15 mmol) was then added. The flask was immersed in an ice bath and methacryloyl chloride (0.15 mL, 1.55 mmol) was added dropwise with stirring. The ice bath was removed and the reaction was maintained at ambient temperature for 7 days under $N_2$. The mixture was concentrated on a rotary evaporator and the crude polymer was chromatographed on silica gel column with dichloromethane mobile phase. The eluent was concentrated using a rotary evaporator and the polymer was isolated by precipitation into cold methanol. The product was isolated by vacuum filtration, rinsed thoroughly with methanol and dried under vacuum at ambient temperature to yield 15.8401 g (78%) of a white solid.

EXAMPLE 3

Synthesis of hydroxyl terminated poly(2-phenylethyl acrylate)

All synthetic manipulations were performed in a $N_2$-filled glove-box. A Schlenk tube containing a PTFE-coated magnetic stirring bar was charged with 0.2438 g (1.700 mmol) of CuBr, 0.6713 g (3.786 mmol) of N,N,N',N',N''-pentamethyldiethylenetriamine, and 7.0941 g (40.26 mmol) of 2-phenylethyl acrylate (PEA). The flask was placed in a 50° C. in an oil bath and 0.2840 g (1.346 mmol) of 2-hydroxyethyl-2-bromoisobutyrate was added. The reaction was maintained at 50° C. for 2 hrs then cooled to room temperature. The product was diluted with tetrahydrofuran and purified by column chromatography. The product was further purified by precipitation from dichloromethane into a large excess of methanol at −50° C. The product was isolated by cold vacuum filtration and rinsed thoroughly with chilled methanol, then dried under vacuum at ambient temperature and resulted in 4.761 g (67%) of a slightly yellow viscous liquid. The molecular weight was determined by GPC in THF against polystyrene standards.

EXAMPLE 4

Synthesis of methacrylate terminated poly(2-phenylethyl acrylate) macromer [3]

An oven dried 3-neck round bottom flask containing a PTFE-coated magnetic stirring bar and equipped with an addition funnel was flushed with $N_2$ and charged with 4.7610 g (0.84 mmol hydroxyl groups based on GPC $M_n$) of $M_n$ 5,676 hydroxyl terminated poly(PEA). Anhydrous dichloromethane (15 mL) was added and the polymer was allowed to dissolve. Triethylamine (0.15 mL, 1.08 mmol) was then added. The flask was immersed in an ice bath and methacryloyl chloride (0.14 mL, 1.45 mmol) was placed in the addition funnel and diluted with 2 mL of dichloromethane. The methacryloyl chloride solution was added dropwise with stirring. Once the addition was complete, the ice bath was removed and the reaction was maintained at ambient temperature for 4 days under $N_2$. The mixture was concentrated on a rotary evaporator and the crude polymer was chromatographed on a basic alumina column with dichloromethane mobile phase. The eluent was transferred to a separatory funnel and washed twice with 1 M HCl, twice with deionized $H_2O$, then saturated NaCl. The organic phase was dried over anhydrous $MgSO_4$, filtered, and the solvent was removed using a rotary evaporator to yield 2.9804 g (63%) of a colorless viscous liquid.

EXAMPLE 5

Copolymerization of 2-phenylethyl methacrylate, 2-phenylethyl acrylate and 1,4-butanediol diacrylate A scintillation vial was charged with 0.6204 g (3.261 mmol, 30.85 wt %) of 2-phenylethyl methacrylate (PEMA), 1.3261 g (7.526 mmol, 65.96 wt %) of 2-phenylethyl acrylate (PEA), 0.0641 g (0.323 mmol, 3.19 wt %) of 1,4-butanediol diacrylate (BDDA), and 0.0264 g (0.161 mmol) of 2-hydroxy-2-methyl-1-phenyl-propan-1-one (Darocur 1173). The solution was mixed thoroughly then de-gassed with $N_2$. The formulation was transferred to polypropylene molds and polymerized by exposure to UV light (~3.0 mW/cm$^2$, 365 nm) for 30 min. The resulting polymer was extracted in acetone for 3 hr, rinsed with fresh acetone and allowed to air dry. The extracted polymer was dried under vacuum at 60° C. for at least 3 hr. The amount of extractables was determined gravimetrically. Representative properties are listed in Table 1.

EXAMPLE 6

Copolymerization of methacrylate terminated poly(2-phenylethyl methacrylate) macromer ($M_n$ 15,460) with 2-phenylethyl acrylate and 1,4-butanediol diacrylate A scintillation vial was charged with 0.6114 g (3.214 mmru, 30.45 wt %) of methacrylate terminated poly(2-phenylethyl methacrylate) (polyPEMA-MA), 1.3336 g (7.568 mmol, 66.42 wt %) of 2-phenylethyl acrylate (PEA), 0.0629 g (0.317 mmol, 3.13 wt %) of 1,4-butanediol diacrylate (BDDA), and 0.0247 g (0.150 mmol) of 2-hydroxy-2-methyl-1-phenyl-propan-1-one (Darocur 1173). The solution was mixed until the polyPEMA-MA dissolved then de-gassed with $N_2$. The formulation was transferred to polypropylene molds and polymerized by exposure to UV light (~3.0 mW/cm$^2$, 365 nm) for 30 min. The resulting polymer was extracted in acetone for 3 hr, rinsed with fresh acetone and allowed to air dry. The extracted polymer was dried under vacuum at 60° C. for at least 3 hr. The amount of extractables was determined gravimetrically. Representative properties are listed in Table 1.

EXAMPLE 7

Copolymerization of methacrylate terminated poly(2-phenylethyl methacrylate) macromer ($M_n$ 18,470) with 2-phenylethyl acrylate and 1,4-butanediol diacrylate A scintillation vial was charged with 0.6114 g (3.214 mmru, 30.47 wt %) of polyPEMA-MA, 1.3259 g (7.525 mmol, 66.09 wt %) of PEA, 0.0690 g (0.348 mmol, 3.44 wt %) of BDDA, and 0.0227 g (0.138 mmol) of Darocur 1173. The solution was mixed to allow dissolution of polyPEMA-MA then de-gassed with $N_2$. The formulation was transferred to polypropylene molds and polymerized by exposure to UV light (~3.0 mW/cm$^2$, 365 nm) for 30 min. The resulting polymer was extracted in acetone for 3 hr, then rinsed with fresh acetone and allowed to air dry. The extracted polymer was dried under vacuum at 60° C. for at least 3 hr. The amount of extractables was determined gravimetrically. Representative properties are listed in Table 1.

EXAMPLE 8

Copolymerization of methacrylate terminated poly(2-phenylethyl methacrylate) macromer ($M_n$ 24,624) with 2-phenylethyl acrylate and 1,4-butanediol diacrylate A scintillation vial was charged with 1.2218 g (6.422 mmru, 30.55 wt %) of polyPEMA-MA, 2.6495 g (15.04 mmol, 66.26 wt %) of PEA, 0.1276 g (0.644 mmol, 3.19 wt %) of BDDA, and 0.0407 g (0.248 mmol, 1.02 wt %) of Darocur 1173. The solution was mixed to allow dissolution of polyPEMA-MA then de-gassed with $N_2$ and filtered through a 1-micron glass fiber filter. The formulation was transferred to polypropylene molds and polymerized by exposure to UV light (~3.0 mW/cm$^2$, 365 nm) for 30 min. The resulting polymer was extracted in acetone for 3 hr, then rinsed with fresh acetone and allowed to air dry. The extracted polymer was dried under vacuum at 60° C. for at least 3 hr. The amount of extractables was determined gravimetrically. Representative properties are listed in Table 1.

TABLE 1

| | Example | | | |
|---|---|---|---|---|
| | 5 | 6 | 7 | 8 |
| PEA (wt %) | 65.96 | 66.42 | 66.09 | 66.26 |
| PEMA (wt %) | 30.85 | — | — | — |
| poly(PEMA)MA (wt %) | — | 30.45 | 30.47 | 30.55 |
| poly(PEMA)MA $M_n$ | — | 15,460 | 18,470 | 24,624 |
| poly(PEMA)MA $M_w/M_n$ | — | 1.14 | 1.15 | 1.15 |
| % BDDA | 3.19 | 3.13 | 3.44 | 3.19 |
| Tensile strength (MPa) | 6.64 ± 0.19 | 7.35 ± 0.54 | 8.19 ± 0.46 | 6.05 ± 1.30 |
| Strain at break (%) | 553 ± 8 | 397 ± 28 | 344 ± 23 | 336 ± 98 |
| Young's modulus | 3.74 ± 0.98 | 6.64 ± 1.27 | 8.27 ± 1.46 | 5.39 ± 1.02 |
| 25% modulus | 4.21 ± 0.43 | 6.14 ± 0.40 | 8.17 ± 0.47 | 5.74 ± 0.54 |
| 100% modulus | 1.87 ± 0.10 | 3.25 ± 0.29 | 4.17 ± 0.11 | 3.07 ± 0.13 |
| Tear resistance (N/mm) | 3.93 ± 0.45 | 5.26 ± 0.78 | 6.01 ± 0.36 | 4.74 ± 0.41 |
| Extractables (%) | 1.02 ± 0.0. | 1.28 ± 0.03 | 2.32 ± 0.16 | 2.58 ± 0.44 |
| $T_g$ (° C.), $2^{nd}$ heating | 7.5 | 6.0 | 7.5 | — |
| Refractive index (25° C.) | 1.5553 ± 0.0002 | 1.5559 ± 0.0002 | 1.5556 ± 0.0001 | 1.5557 ± 0.0002 |

The data in Table 1 demonstrates that the addition of macromer (3) improves the strength properties of soft acrylic polymers allowing increased distortion without fracture. For example, in Table 1, a 2-phenylethyl acrylate-poly(PEMA)MA graft copolymer (Ex. 6) has increased tensile strength and tear resistance as compared to a statistical copolymer of 2-phenylethyl acrylate and 2-phenylethyl methacrylate of identical monomer feed ratio (Ex. 5).

EXAMPLE 9

Copolymerization of 2-phenylethyl methacrylate, 2-phenylethyl acrylate and 1,4-butanediol diacrylate A scintillation vial was charged with 2.5011 g (13.15 mmol, 25.0 wt %) of PEMA, 7.4014 g (42.00 mmol, 74.0 wt %) of PEA, 0.1007 g (0.508 mmol, 1.00 wt %) of BDDA, and 0.1006 g (0.613 mmol) of Darocur 1173. The solution was mixed thoroughly then de-gassed with $N_2$. The formulation was transferred to polypropylene molds and polymerized by exposure to UV light (~3.0 mW/cm², 365 nm) for 30 min. The resulting polymer was extracted in acetone for 3 hr, rinsed with fresh acetone and allowed to air dry. The extracted polymer was dried under vacuum at 60° C. for at least 3 hr. The amount of extractables was determined gravimetrically. Representative properties are listed in Table 2.

EXAMPLE 10

Copolymerization of methacrylate terminated poly(2-phenylethyl methacrylate) macromer ($M_n$ 18,470) with 2-phenylethyl acrylate and 1,4-butanediol diacrylate A scintillation vial was charged with 0.5011 g (2.634 mmru, 24.85 wt %) of polyPEMA-MA, 1.4935 g (8.476 mmol, 74.07 wt %) of PEA, 0.0216 g (0.109 mmol, 1.07 wt %) of BDDA, and 0.0212 g (0.129 mmol) of Darocur 1173. The solution was mixed to allow dissolution of polyPEMA-MA then de-gassed with $N_2$. The formulation was transferred to polypropylene molds and polymerized by exposure to UV light (~3.0 mW/cm², 365 nm) for 30 min. The resulting polymer was extracted in acetone for 3 hr, then rinsed with fresh acetone and allowed to air dry. The extracted polymer was dried under vacuum at 60° C. for at least 3 hr. The amount of extractables was determined gravimetrically. Representative properties are listed in Table 2.

EXAMPLE 11

Copolymerization of methacrylate terminated poly(2-phenylethyl methacrylate) macromer ($M_n$ 24,624) with 2-phenylethyl acrylate and 1,4-butanediol diacrylate A scintillation vial was charged with 1.0010 g (5.262 mmru, 24.96 wt %) of polyPEMA-MA, 2.9701 g (16.86 mmol, 74.06 wt %) of PEA, 0.0393 g (0.198 mmol, 0.98 wt %) of BDDA, and 0.0385 g (0.234 mmol, 0.96 wt %) of Darocur 1173. The solution was mixed to allow dissolution of polyPEMA-MA then de-gassed with $N_2$ and filtered through a 1-micron glass fiber filter. The formulation was transferred to polypropylene molds and polymerized by exposure to UV light (~3.0 mW/cm², 365 nm) for 30 min. The resulting polymer was extracted in acetone for 3 hr, then rinsed with fresh acetone and allowed to air dry. The extracted polymer was dried under vacuum at 60° C. for at least 3 hr. The amount of extractables was determined gravimetrically. Representative properties are listed in Table 2.

TABLE 2

| | Example | | |
|---|---|---|---|
| | 9 | 10 | 11 |
| PEA (wt %) | 74.00 | 74.08 | 74.06 |
| PEMA (wt %) | 25.00 | — | — |
| poly(PEMA)MA (wt %) | — | 24.85 | 24.96 |
| poly(PEMA)MA $M_n$ | — | 18,470 | 24,624 |
| poly(PEMA)MA $M_w/M_n$ | — | 1.15 | 1.15 |
| % BDDA | 1.00 | 1.07 | 0.98 |

TABLE 2-continued

| | Example | | |
|---|---|---|---|
| | 9 | 10 | 11 |
| Tensile strength (MPa) | 3.17 ± 0.53 | 5.58 ± 0.38 | 4.89 ± 0.51 |
| Strain at break (%) | 948 ± 64 | 1033 ± 29 | 1158 ± 47 |
| Young's modulus | 0.70 ± 0.24 | 2.00 ± 0.35 | 1.67 ± 0.27 |
| 25% modulus | 0.65 ± 0.20 | 2.51 ± 0.27 | 1.56 ± 0.31 |
| 100% modulus | 0.41 ± 0.06 | 1.11 ± 0.07 | 0.90 ± 0.05 |
| Tear resistance (N/mm) | 2.17 ± 0.33 | 3.08 ± 0.44 | 3.08 ± 0.02 |
| Extractables (%) | 2.69 ± 0.25 | 3.61 ± 0.06 | 4.98 ± 0.13 |
| $T_g$ (° C.), $2^{nd}$ heating | — | 3.0 | — |
| Refractive index (25° C.) | 1.5522 ± 0.0006 | 1.5561 ± 0.0001 | 1.5560 ± 0.0001 |

The data in Table 2 also demonstrate that the addition of macromer [3] improves the strength properties of soft acrylic polymers allowing increased distortion without fracture. For example, in Table 2, a 2-phenylethyl acrylate-poly(PEMA) MA graft copolymer (Ex. 10) has increased tensile strength and tear resistance as compared to a statistical copolymer of 2-phenylethyl acrylate and 2-phenylethyl methacrylate of identical monomer feed ratio (Ex. 9).

EXAMPLE 12

Copolymerization of methacrylate terminated poly (2-phenylethyl methacrylate) macromer ($M_n$ 6,300) with 2-phenylethyl acrylate, 2-(2-methoxyethoxy) ethyl methacrylate and 1,4-butanediol diacrylate A 20-mL scintillation vial was charged with 0.8072 g of poly(2-phenylethyl methacrylate) macromer, 2.5693 g of 2-phenylethyl acrylate (PEA), 0.6131 g of 2-(2-methoxyethoxy)ethyl methacrylate (MEEMA), and 0.0410 g of 1,4-butanediol diacrylate (BDDA). The vial was closed and agitated to allow the macromonomer to dissolve. The monomer mixture was filtered through a 1.0-micron glass fiber membrane. The formulation was de-gassed by bubbling $N_2$ through the monomer mixture. Di(4-tert-butylcyclohexyl) peroxydicarbonate (Perkadox 16S) was added (0.0202 g) and the solution was mixed thoroughly. The monomer mixture was dispensed into vacuum de-gassed polypropylene molds under a $N_2$ atmosphere. The filled molds were placed in a 70° C. mechanical convection for 1 hr, then post-cured at 110° C. for 2 hrs. The product was removed from the polypropylene molds and residual monomer was removed by acetone extraction at room temperature. The product polymer was dried under vacuum at 60° C.

All of these copolymers (Examples 5-12) have excellent clarity as cast.

The graft copolymers of the present invention also exhibit a reduced surface tackiness as compared to statistical copolymers of identical feed composition, and this improves the manufacturability and manipulation of IOLs.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A polymeric ophthalmic or otorhinolaryngological device material comprising
   a) a monofunctional acrylate or methacrylate monomer (1);
   b) a difunctional acrylate or methacrylate cross-linking monomer (2), and
   c) an acrylate or methacrylate terminated aromatic functional methacrylic or acrylic macromer (3) or an acrylate or methacrylate terminated aromatic functional methacrylic or acrylic macromer (4):

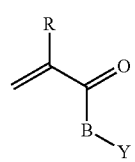
[1]

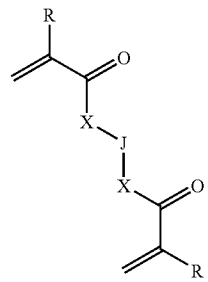
[2]

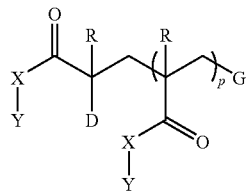
[3]

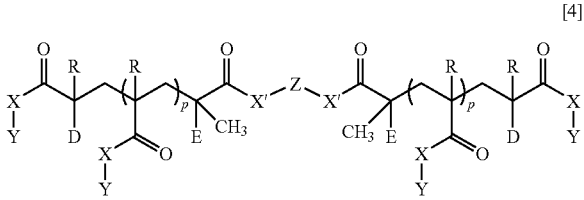
[4]

wherein
B=$O(CH_2)_n$, $NH(CH_2)_n$, or $NCH_3(CH_2)_n$;
D=Cl, Br, H, or —$CH_2C(=CH_2)C(O)XY$;
E=H or $CH_3$;
G=H, $C(E)(CH_3)C(O)X(CH_2)_nH$, $C(E)(CH_3)C(O)X(CH_2CH_2O)_nCH_3$, or $C(E)(CH_3)C(O)XZ'X'C(O)C(R')=CH_2$;
R, R' independently=H, $CH_3$, or $CH_2CH_3$;
X, X' independently=$O(CH_2)_n$, $NH(CH_2)_n$, $NCH_3(CH_2)_n$, $O(CH_2CH_2O)_nCH_2$, $O(CH_2CH_2CH_2O)_nCH_2$, $O(CH_2CH_2CH_2CH_2O)_nCH_2$, or nothing;
J=$(CH_2)_a$, $O(CH_2CH_2O)_b$, O, or nothing;
n=0-6;
Y=$C_6H_5$, $(CH_2)_mH$, or $(CH_2)_mC_6H_5$;
m=0-12;
Z, Z' independently=—$(CH_2)_a$—, —$(CH_2CH_2O)_a$—, —$(CH_2CH_2CH_2CH_2O)_a$—, —$C_6H_4$—, —$C_6H_4C(CH_3)(CH_3)C_6H_4$—, or —$[(CH(CH_2CH_3)CH_2)(CH_2CH_2)]_q$—;

a=1-12;
b=1-24;
p=5-400; and
q=1-80; and
wherein the total amount of macromers (3) and (4) is at least 5% (w/w) of the device material, the total amount of monomer (1) is at least 35% (w/w) of the device material, for macromer (3) is such that $M_n$ for macromer (3) is 5,000-50,000 and p for macromer (4) is such that $M_n$ for macromer (4) is 1,000-10,000.

2. The polymeric device material of claim 1 wherein the monomer of formula (1) is selected from the group consisting of those wherein
R=H, B=O(CH$_2$)$_2$, Y=C$_6$C$_5$;
R=H, B=O(CH$_2$)$_3$, Y=C$_6$H$_5$; and
R=CH$_3$, B=O(CH$_2$)$_4$, Y=C$_6$H$_5$.

3. The polymeric device material of claim 1 wherein the monomer of formula (2) is selected from the group consisting of those wherein:
R=H, X=OCH$_2$, J=(CH$_2$)$_2$,
R=CH$_3$, X=OCH$_2$, J=nothing; and
R=CH$_3$, X=nothing, J=O(CH$_2$CH$_2$O)$_b$, where b>10.

4. The polymeric device material of claim 1 wherein the monomer of formula (2) is selected from the group consisting of ethylene glycol dimethacrylate; diethylene glycol dimethacrylate; 1,6-hexanediol dimethacrylate; 1,4-butanediol dimethacrylate; poly(ethylene oxide)dimethacrylate (number average molecular weight 600-1000); and their corresponding acrylates.

5. The polymeric device material of claim 1 wherein the macromer of formula (3) is selected from the group consisting of those wherein
R=H or CH$_3$;
G=C(E)(CH$_3$)C(O)X'Z'X'C(O)C(R')=CH$_2$;
X=O(CH$_2$)$_2$ and X'=O;
Y=C$_6$H$_5$;
E=CH$_3$; and
Z and Z'=(CH$_2$)$_2$.

6. The polymeric device material of claim 1 wherein the macromer of formula (3) is selected from the group consisting of those wherein
R=H or CH$_3$;
D=—CH$_2$C(=CH$_2$)C(O)XY;
X=O(CH$_2$)$_2$;
Y=C$_6$H$_5$;
E=CH$_3$; and
Z and Z'=(CH$_2$)$_2$.

7. The polymeric device material of claim 1 wherein the macromer of formula (4) is selected from the group consisting of those wherein:
R=H or CH$_3$;
X=O(CH$_2$)$_2$;
Y=C$_6$H$_5$;
E=CH$_3$;
D=CH$_2$C(=CH$_2$)C(O)XY;
X'=O; and
Z'=(CH$_2$)$_2$.

8. The device material of claim 1 wherein the device material comprises a monomer of formula (1), a monomer of formula (2), a macromer of formula (3), and a macromer of formula (4).

9. The device material of claim 8 wherein the total amount of monomer of formula (1) is 65-85% (w/w).

10. The device material of claim 1 wherein the total amount of the monomer of formula (2) does not exceed 15% (w/w).

11. The device material of claim 10 wherein the total amount of monomer of formula (2) is less than 3% (w/w).

12. The device material of claim 1 wherein the total amount of macromers (3) and (4) is 5-55% (w/w).

13. The device material of claim 1 wherein the device material comprises a macromer of formula (3) having R=CH$_3$ or CH$_2$CH$_3$, the amount of macromer (3) in the device material is 5-35%, and the number average molecular weight of macromer (3) is 10,000-25,000.

14. The device material of claim 1 wherein the device material further comprises an ingredient selected from the group consisting of a polymerizable UV absorber and a polymerizable colorant.

15. The device material of claim 1 wherein the device material has a refractive index in the dry state of at least 1.47.

16. The device material of claim 1 wherein the device material has a continuous phase glass transition temperature less than 25° C.

17. The device material of claim 1 wherein the device material has an elongation of at least 150% and a Young's modulus of less than 6.0 MPa.

18. An ophthalmic or otorhinolaryngological device comprising the device material of claim 1 wherein the ophthalmic or otorhinolaryngological device is selected from the group consisting of intraocular lenses; contact lenses; keratoprostheses; corneal inlays or rings; otological ventilation tubes; and nasal implants.

19. An intraocular lens comprising the device material of claim 1.

* * * * *

UNITED STATES PATENT AND TRADEMARK OFFICE
CERTIFICATE OF CORRECTION

PATENT NO. : 7,652,076 B2 Page 1 of 1
APPLICATION NO. : 11/451097
DATED : January 26, 2010
INVENTOR(S) : Schlueter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 888 days.

Signed and Sealed this

Twenty-third Day of November, 2010

David J. Kappos
*Director of the United States Patent and Trademark Office*